United States Patent [19]

Sawai et al.

[11] Patent Number: 4,952,568
[45] Date of Patent: Aug. 28, 1990

[54] REMEDIES AND PREVENTIVES FOR DIABETIC DISEASES

[75] Inventors: Kiichi Sawai, Funabashi; Masayasu Kurono, Mieken; Hiromoto Asai, Nagoya; Takahiko Mitani; Kazumasa Nakano, both of Mie; Naohisa Ninomiya, Nagoya, all of Japan

[73] Assignee: Sanwa Kagaku Kenkyusho Co., Ltd., Higashi, Japan

[21] Appl. No.: 348,922

[22] Filed: May 8, 1989

[30] Foreign Application Priority Data

May 19, 1988 [JP] Japan .................................. 63-122347

[51] Int. Cl.⁵ .............................................. A61K 33/66
[52] U.S. Cl. .................................... 514/103; 514/102; 514/866
[58] Field of Search .......................... 514/103, 866, 102

[56] References Cited

U.S. PATENT DOCUMENTS 4,847,082  7/1989  Sabin .................................... 514/103

Primary Examiner—Frederick E. Waddell
Attorney, Agent, or Firm—Armstrong, Nikaido, Marmelstein, Kubovcik & Murray

[57] ABSTRACT

Remedies, preventives and functional diets for diabetic diseases, esp., diabetes, contain phytic acid or its salt or salts. The salt of phytic acid is a non-toxious metal salt, or a non-toxious salt with an organic base, a basic amino acid or an organic ester residue, and has a compositional form together with or separately from phytic acid.

4 Claims, 1 Drawing Sheet

CHANGES OF FREE FATTY ACIDS WITH CHANGES IN DOSAGES

RESULTS OF INDUCTION-TESTING-WITH-TIME

REMEDIES AND PREVENTIVES FOR DIABETIC DISEASES

BACKGROUND OF THE INVENTION

1. Field of the Invention

The present invention relates to a pharmaceutic material as well as a functional diet for alleviating diabetic diseases, particularly preventing and curing diabetes, which contains phytic acid or its salt or salts as an effective component.

2. Statement of the Prior Art

Sugar metabolic disease, diabetes is a disease that is induced by improper meals and obesity by way of genetic dispositions and, upon lingering, is complicated by vascular disorders or other diseases.

The treatments for such diseases are carried out with a view to normalizing sugar metabolism, suppressing the progress thereof and preventing complications, esp., vascular complications. In real treatments, (1) appropriate dietary cures, (2) the administration of insulin and orally administrable diabetic medicines and (3) the administration of complication remedies are applied in combination.

On the other hand, phytic acids widely appear in plants as calcium and magnesium salts, sometimes a potassium salt. For instance, rice bran contains as high as 9.5 to 14.5 % of phytic acid, and provides a starting material for commercial phytic acid and myoinositol deriving therefrom.

Phytic acid and its salt have been used in wide applications; in pharmaceutical applications, calcium phytate has been used as a calcium augmentor, rice bran itself and sodium phytate as a preventive for calcium calculuses, and potassium phytate for the treatment of hypercalcemia and hyper-calciurea of sarcoidosis patients. They have also been utilized in various other fields as fermentative aids for brewing sake and wine, metal removers making use of the chelating action of phytic acid, antioxidants in the presence of iron and calcium ions and anticorrosives for metals.

However, it has not been reported to date that phytic acid and its salts may be effective for a lowering of blood sugar and be used as preventives and remedies for arteriosclerosis that is a diabetic complication.

SUMMARY OF THE INVENTION

In view of the foregoing, the present invention has for its general object to provide pharmaceutical materials effective for a lowering of blood sugar, remedies and preventives for arteriosclerosis caused by diabetes, and functional diets available even to sound individuals in view of health.

The inventors have discovered that when orally administered in the process of nutrition experiments, phytic acid serves to reduce body smells, especially, foul breath, perspiratory smell and urinous smell. In particular, detailed studies of the effects of removal of garlic breath has revealed that this is accomplished by the enzymatic inhibition or biometabolism promotion of phytic acid, and has further indicated that phytic acid is effective for the inhibition of glycosuria and a lowering of lipid.

A primary object of the present invention accomplished on the basis of the aforesaid findings is to provide preventives and remedies as well as functional diets for diabetic diseases, which contain phytic acid and its salt or salts as an effective component.

The present invention relates to alleviative, remedial and preventive effects obtained when phytic acid and its salt(s) are applied to the sugar metabolism of humans, esp., diabetes and arteriosclerosis that is a diabetic complication and to functional diets making use of such effects. Phytic acid and its salt are so tasteless and odorless that their oral administration is easily achieved. Thus, they may be expected to produce their effects by being mixed with eatables and drinkables or sprinkled over or blended with meals, or orally administered in the form of powders or granules.

According to the present invention, phytic acid and its salt(s) may suitably be administered to humans, generally adults, in a dosage of 1 to 100 mg/kg/day, although depending upon the conditions of patients and the type of preparations.

The phytates usable in the present invention may include innoxious metal salts as well as innoxious salts with organic salts, basic amino acids and organic ester residues such as those represented by potassium phytate, sodium phytate, ammonium phytate, arginine phytate, ornithine phytate, lysine phytate, histidine phytate, monoethanolamine phytate, diethanolamine phytate, triethanolamine phytate and glucamine phytate. The phytates may also take a compositional form together with or separately from phytic acid.

In various preparations, phytates and their mixtures in a pH range of 6 to 8 may generally be selectively used depending upon the purposes of pharmaceutics as well as functional diets because of their strong acidity.

The number of moles of various bases required to regulate one mole of phytic acid to pH 6 to 8 is shown in Table 1.

TABLE 1

| Bases | pH 6.00 | 7.00 | 8.00 |
|---|---|---|---|
| NaOH | 7.34 | 8.21 | 8.94 |
| KOH | 7.34 | 8.23 | 8.94 |
| LiOH | 7.41 | 8.38 | 9.30 |
| NH$_4$OH | 7.61 | 8.55 | 9.45 |
| HOC$_2$HCH$_2$NH$_2$ | 7.72 | 8.68 | 9.52 |
| (HOCH$_2$CH$_2$)$_2$NH | 7.54 | 8.45 | 9.31 |
| (HOCH$_2$CH$_2$)$_3$N | 7.20 | 8.53 | 12.1 |
| N-Methylglucamine | 7.62 | 8.49 | 9.25 |
| L-Arginine | 7.79 | 8.67 | 9.60 |
| L-Lysine | 8.01 | 8.98 | 10.0 |
| L-Histidine | 11.3 | — | — |

In sum, the desired effects of the preparations in the present invention are easily obtained by oral administration, since they contain phytic acid and its salt(s) as the main component.

Further, the preparations in or by the present invention may be administered by way of an oral route, since, whether liquid or solid, phytic acid and its salt(s) are effective.

Still further, the compositions in the present invention are of safety so high that they are continuously usable, and are effective for alleviating chronic alcoholism by their continued use or administration.

BRIEF DESCRIPTION OF THE DRAWINGS

The present invention will now be described with reference to the drawings, which are given for the purpose of illustration alone, and in which.

EXAMPLES

Figure 1:
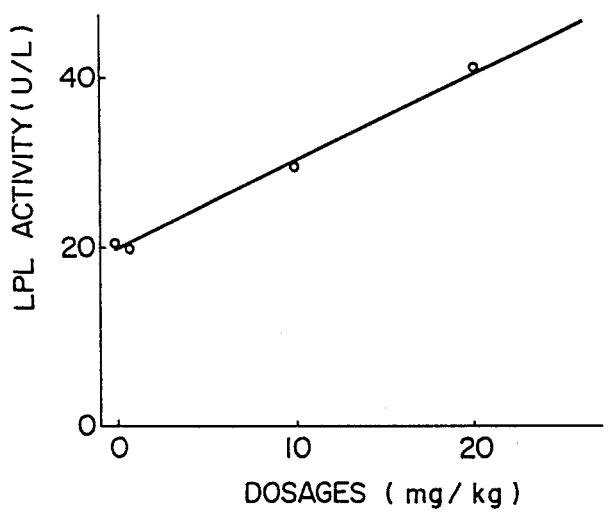
FIG. 1 is a graphical view illustrating a change of free fatty acids in blood with a change in the amount of phytic acid administered.

The present invention will now be explained in detail with reference to the following examples, which are give for the purpose of illustration alone.

EXAMPLE 1

Composition a

Twenty-nine (29) g of sodium hydroxide and a suitable amount of refined water are added to 660 g of phytic acid (as an anhydride) to obtain a liquid regulated to pH 6.

Composition b

Four hundred and twelve (412) g of potassium hydroxide and a suitable amount of refined water are added to 660 g of phytic acid (as an anhydride) to obtain a liquid regulated to pH 6.

Composition c

One hundred and seventy-seven (177) g of lithium hydroxide and a suitable amount of refined water are added to 660 g of phytic acid (as an anhydride) to obtain a liqiud regulated to pH 6.

Composition d

Five hundred and eighty-one (581) g of ethanolamine and a suitable amount of refined water are added to 660 g of phytic acid (as an anhydride) to obtain a liquid regulated to pH 8.

Composition e

Nine hundred and seventy-nine (979) g of diethanolamine and a suitable amount of refined water are added to 660 g of phytic acid (as an anhydride) to obtain a liquid regulated to pH 8.

Composition f

One thousand eight hundred and five (1,805) g of triethanolamine and a suitable amount of refined water added to 660 g of phytic acid (as an anhydride) to obtain a liquid adjusted to pH 8.

Composition g

One thousand six hundred and fifty-seven (1657) g of N—methylglucamine and a suitable amount of refined water are added to 660 g of phytic acid (as an anhydride) to obtain a liquid adjusted to pH 7.

Composition h

One thousand five hundred and ten (1510) g of L-arginine and a suitable amount of refined water are added to 660 g of phytic acid (as an anhydride) to obtain a liquid adjusted to pH 7.

Composition i

One thousand seven hundred and fifty-three (1753)g of L—histidine and a suitable amount of refined water are added to 660 g of phytic acid (as an anhydride) to obtain a liquid adjusted to pH 6.

Composition j

One hundred and sixteen (116) g of sodium hydroxide, 478 g of potassium hydroxide, 6.08 g of potassium chloride (as a dihydrate), 157 g of disodium hydrogen phosphate (as an anhydride) and a suitable amount of refined water are added to 660 g of phytic acid (as an anhydride) to obtain a liquid adjusted to pH 9.

These compositions a to j may be powderized crystallization or the addition of a vehicle.

These compositions a to j may also be formed into compositions in the form of liquids or powders, from which the preparations may be obtained.

EXAMPLE 3

The composition j obtained in Example 2 was formed into a composition, from which various preparations were obtained.

Composition A for Preparations

Lactose is added to the composition j (containing 200 mg of phytic acid) to obtain a total of 1000 mg of a composition.

Composition B for Preparations

Lactose is addded to the composition j (containing 100mg of phytic acid) to obtain a total of 1000 mg of a composition.

Composition C for Preparations

Refined water is added to the composition j (containing 100 mg of phytic acid) to obtain a total of 1000 mg of a composition.

Composition D

Light silicic anhydride is added to the composition j (containing 200 mg of phytic acid), followed by drying, which gives a total of 1000 mg of a composition.

PRODUCTION EXAMPLES OF PREPARATIONS

Production Example 1

(Erixir)

| | | |
|---|---|---|
| Composition C | 100 g | (10 g calculated as phytic acid) |
| Compound orange extract | 24 ml | |
| Ethanol | 400 ml | |
| Glycerine | 400 ml | |
| Refined water | Total: 1000 ml | |

Predetermined amounts of the aforesaid components are uniformly mixed together to obtain a colorless and clear erixir preparation. A five-milliliter dosage of this erixir preparation contains 50 mg of phytic acid.

Production Example 2

(Capsule)

| | |
|---|---|
| Composition A | 200 mg (40 mg calculated as phytic acid) |
| Lactose | 20 mg |
| Corn starch | 38 mg |
| Magnesium stearate | 2 mg |

Predetermined amounts of the aforesaid components are uniformly mixed together and packed in No. 2 capsules. One such capsule contains 40 mg of phytic acid.

Production Example 3

(Granule)

| Composition A | 600 mg | (120 mg calculated as phytic acid) |
|---|---|---|
| Lactose | 140 mg | |
| Corn starch | 250 mg | |
| Hydroxypropylcellulose | 10 mg | |

Predetermined amounts of the aforesaid components are uniformly mixed together, and the mixture is then wet-granulated with water and ethanol into granules. One hundred and twenty (120) mg of phytic acid are contained in an one-gram dosage of such granules.

Production Example 4

(Powder)

The composition A is divided and heat-sealed in aluminum to obtain wrappers each of 1.5 g.

Production Example 5

(Tablet)

| Composition A | 100 mg | (20 mg calculated as phytic acid) |
|---|---|---|
| Corn starch | 19 mg | |
| Crystalline cellulose | 30 mg | |
| Magnesium stearate | 1 mg | |

Predetermined amounts of the aforesaid components are uniformly mixed together, and the mixture is then compressed into tablets each of 7 mm in diameter and 150 mg in weight. One such tablet contains 20 mg of phytic acid.

Production Example 6

(Syrup)

| Composition C | | 50 g | (5 g calculated as phytic acid) |
|---|---|---|---|
| White sugar | | 300 g | |
| D-sorbitol (70%) | | 250 g | |
| Methyl p-oxybenzoate | | 0.3 g | |
| Propyl p-oxybenzoate | | 0.15 g | |
| Sodium citrate | | 10 g | |
| Perfume | | 1.5 g | |
| Refined water | Total: | 1000 ml | |

Predetermined amounts of the aforesaid components are dissolved and mixed together into a colorless and clear syrup. One hundred (100) mg of phytic acid is contained in a twenty-milliliter dosage of this syrup.

Production Example 7

(Dry Syrup)

| Composition B | 100 mg (10 mg calculated as phytic acid) |
|---|---|
| Sodium citrate | 2.4 mg |
| Citric anhydride | 2.2 mg |
| Tragacanth powders | 2.7 g |
| White sugar | suitable amount |
| Hydroxypropylcellulose | 3.0 mg |
| Perfume | slight amount |
| Perfume | slight amount |

Predetermined amounts of the aforesaid components are uniformly mixed together, and are then wet-granulated with water and ethanol into a dry syrup. An one (1)-gram dosage of this syrup contains 10 mg of phytic acid.

Production Example 8

(Troche)

| Composition A | 100 mg (20 mg calculated as phytic acid) |
|---|---|
| White sugar | 870 mg |
| Lactose | 20 mg |
| Magnesium stearate | 10 mg |

Of the aforesaid components the composition A and white sugar are uniformly mixed together in the respective amounts of 100 g and 870 g, and are then wet-granulated with water and ethanol, followed by drying at a temperature of lower than 35° C. Added to the dried product are 20 g of lactose and 10 g of magnesium stearate to obtain troches each of 15 mm in diameter and 1 g in weight. One such troche contains 20 mg of phytic acid.

Production Example 9

(Candy)

| Composition B | 100 mg (10 mg calculated as phytic acid) |
|---|---|
| White sugar | 2400 mg |
| Starch syrup | 1500 mg |
| Perfume | slight amount |

Of the aforesaid components, 240 g of white sugar and 150 g of starch syrup are mixed with 100 g of refined water. After melting by heating, the mixture is sieved out for the removal of foreign matters. The resulting liquid is concentrated under pressure with the application of heat for dehydration to prepare a starch syrup dough having a moisture content of 2 to 3% at 130° to 150° C. Added to this dough are 10 g of the composition B and a slight amount of perfume, and the product is molded to obtain candies each of 4 g in weight. Each candy contains 10 mg of phytic acid.

Production Example 10

(Limonada)

| Composition C | | 3 g (300 mg calculated as phytic acid) |
|---|---|---|
| Syrup | | 2.5 ml |
| Refined water | Total: | 30 ml |

Predetermined amounts of the aforesaid components are uniformly mixed together into limonadas. A thirty (30)-milliliter dosage of such limonadas contains 300 mg of phytic acid.

Production Example 11

(Granule)

| Composition D | 500 mg (100 mg calculated as phytic acid) |
|---|---|
| Garlic powders | 750 mg |
| Lactose | suitable amount |

Predetermined amounts of the aforesaid components are uniformly mixed together, and are then wet-granulated with water and ethanol into granules. One hundred (100) mg of phytic acid is contained in an 1.5-gram dosage of such granules.

Production Example 12

(Drinkable Solution)

| Composition C | 1 g (100 mg calculated as phytic acid) |
|---|---|
| Mel | 0.5 g |
| White sugar | 2.0 g |
| Citric acid | suitable amount |
| Sodium citrate | suitable amount |
| Peppermint | slight amount |
| Refined water | suitable amount |

Predetermined amounts of the aforesaid components were uniformly mixed together into a colorless and clear internal liquid preparation. A thirty (30)-milliliter dosage of this liquid preparation contains 100 mg of phytic acid.

Production Example 13

(Garlic Flavoring)

| Composition D | 0.285 g (0.1 g calculated as phytic acid) |
|---|---|
| Avisel | 0.18 g |
| Garlic powders | 0.75 g |
| Light silicic anhydride | 0.256 g |
| starch | suitable amounts |

Predetermined amounts of the aforesaid components are granulated by a conventional method.

Stability Testing

The preparations according to Production Examples 1 to 10 were subjected to stability testing to measure the amount of residual phytic acid. The results are set forth in Table 2.

TABLE 2

Amounts of Residual Phytic Acid in the Stability Testing of the Preparations According to the Production Examples (% with respect to the specified contents)

| Samples | Storage Vessels | At the beginning of storage | After 3 weeks at 60° C. |
|---|---|---|---|
| P.Ex. 1A* | Glass Bottle | 100.5 | 101.2 |
| P.Ex. 2B* | PTP | 101.4 | 99.4 |
| P.Ex. 3C* | Aluminium Wrapper | 100.1 | 100.0 |
| P.Ex. 4D* | Aluminium Wrapper | 100.9 | 102.1 |
| P.Ex. 5E* | PTP | 99.2 | 99.8 |
| P.Ex. 6F* | Glass Bottle | 102.1 | 100.3 |
| P.Ex. 7G* | Aluminium Wrapper | 100.6 | 100.1 |
| P.Ex. 8H* | Aluminium SP | 99.7 | 100.5 |
| P.Ex. 9I* | Aluminium Bag | 99.9 | 99.2 |
| P.Ex. 10J* | Glass Bottle | 102.1 | 100.9 |
| P.Ex. 11K* | Aluminium Wrapper | 100.3 | 100.1 |
| P.Ex. 12L* | Glass Bottle | 100.1 | 99.8 |

A*: Erixir, B*: Capsule, C*: Granule, D*: Powder, E*: Tablet,
F*: Syrup, G*: Dry Syrup, H*: Troche, I*: Candy, J*: Limonada,
K*: Granule, L*: Drinkable Solution.

EXAMPLE 2—TESTING EXAMPLES

1. Effect on the Suppression of Glycosuria in Mice with Alloxan Diabetes (a) Test Animals and Procedures Used for testing were three groups of ddy male mice weighing about 20 g (21 to 23 g) and fasted for three hours, five per group. The testing control was intraperitoneally administrated with sodium phytate in a ratio of 100 to 200 mg/kg, while the normal and control groups were dosed with physiological saline in a ratio of 10 ml/kg. The control group was also administrated with alloxan in a ratio of 75 mg/kg through the tail's veins. Twenty-four hours after the administration, blood was gathered under etherization from the descending arotae to measure the concentrations of blood sugar and ketone body (acetoacetic acid and $\beta$-hydroxybutyric acid) in plasma with an autoanalyzer (Hitachi, Model 705).

(b) Test Reagents (1) Used for the measurement of blood sugar was Glucose HA Test WAKO (put by Wako Junyaku Co., Ltd. on the market).

(2) Used for the measurement of acetoacetic acid was Ketone Test A Sanwa (sold by Sanwa Chemical Institute Co., Ltd.).

(3) Used for the measurement of $\beta$-hydroxybutyric acid was Ketone Test B Sanwa (sold by Sanwa Chemical Institute Co., Ltd.).

(c) Test Results

The results are set forth in Table 3, from which it is found that the concentration of blood sugar tends to drop by the administration of 100 mg/kg of sodium phytate, and such a tendency turns significant in 200 mg/kg. It is also noted that the concentration of ketone body tends to drop in either case. This indicates that sodium phytate is effective to suppress glycosuria.

TABLE 3

| | Dosage of Na Phytate in mg/kg | Sugar in mg/dl | Ketone Body in $\mu$mol/l (1) | (2) |
|---|---|---|---|---|
| Normal Group | | 189 | 0 | 114 |
| Control Group | - | 548 ± 46 | 44 | 635 |
| Test Group | 100 | 291 ± 117 | 5 | 194 |
| Test Group | 200 | 147 ± 14 | 14 | 154 |

2. Induction of Lipoprotein lipase (LPL for short)—effective to cure secondary diseases developed by diabetes (a) Test Animals and Procedures In a range of 1 to 50 mg, sodium phytate was administered under anesthesia to four groups of Wistar rats weight 190 to 200 g and fasted for 12 hours or longer, five per group. Five minutes after the administration, blood was gathered from the descending arotae. Sodium citrate was added to the collected blood to regulate its final concentration to 3 mg/ml, which was in turn centrifuged to obtain plasma.

(b) Test Procedures

The activity of LPL in the obtained plasma was determined by the measurement of librating fatty acids.

The free fatty acids were measured with NEFAC Test Wako-Kit (put by Wako Junyaku Co., Ltd. on the market).

(c) Test Results (1) The results of changes in the free fatty acids with changes in the dosage are shown in FIG. 1.

By measurement, it has been found that the free fatty acids are induced depending upon the amount of sodium phytate in the range of 1 to 50 mg/kg/weight, but the animals are killed down in a dosage exceeding 50 mg/kg/weight.

(2) Results of Induction-with-time of Free Fatty Acids

Figure 2:
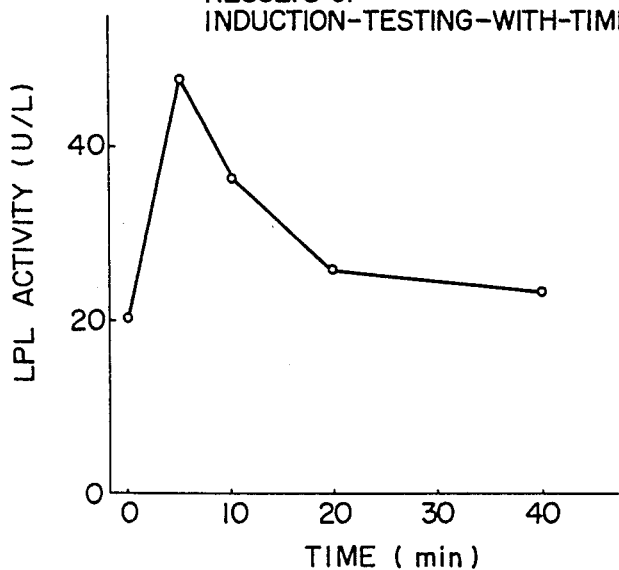
FIG. 2 is a graphical view illustrating the results of induction-testing-with-time of free fatty acids after the administration of phytic acid.

With an intravenous injection of sodium phytate in an dosage of 20 mg/kg/weight, the maximum induction of LPL occurred five minutes after the injection, and was sustained over about 40 minutes, as can be understood from the results shown in FIG. 2.

From the foregoing results, it has been found that the present invention is effective to lower lipid levels.

3. Organoleptical Comparison Test

For organoleptic comparison testing on whether the taste, edibleness and the smell are good or bad, beefsteaks cooked with 0.5 g (33 mg calculated as phytic acid) of the garlic flavoring preparation according to Production Example 13 and other seasonings were fed to a 20-member panel simultaneously with those without phytic acid. The results are shown in Table 4.

TABLE 4

|  | Indistinguishable from pytic acid-free steaks | Better than pytic acid-free steaks | Bad |
| --- | --- | --- | --- |
| Taste | 6 | 14 | 0 |
| Edibleness | 5 | 15 | 0 |
| Smell | 1 | 19 | 0 |

From the above results, it has been found that phytic acid excels in the taste, edibleness and the smell, and is effective as a food flavoring material.

4. Organoleptic Test

Thirty (30) ml (100 mg calculated as phytic acid) of the drinkable solution of Production Example 12 was continuously administered to three diabetic patients once a day for 7 days, and a questionnaire was conducted on its drinkability and effects. The results are shown in Table 5.

TABLE 5

|  |  | Good | Indistinguishable |
| --- | --- | --- | --- |
| Drinkability |  | 3 | 0 |
| Effects | (a) Recovery from fatigue | 2 | 1 |
|  | (b) Amelioration of conditions | 3 | 0 |

It is here to be noted that this drinkable solution was administrated to the patients, while suggesting that it was a healthful diet effective for diabetes. Although it may not be possible to deduce from such results any significant comment on the workings of phytic acid, it is believed that phytic acid is organoleptically effective as one of food additives.

What is claimed is:

1. A method for alleviating the symptoms of diabetes in an animal afflicted with diabetes which comprises administering to the animal phytic acid or a non-toxic salt thereof in an amount effective to lower the animal's blood sugar level.

2. A method according to claim 1, wherein the salt is a salt of phytic acid with an amino acid.

3. A method according to claim 1, wherein the salt is potassium phytate, sodium phytate or ammonium phytate.

4. A method according to claim 1, wherein the phytic acid or non-toxic salt thereof is administered orally at a dosage of 1 to 100 mg/kg/day.

* * * * *